United States Patent [19]

Conrad et al.

[11] 4,191,688

[45] Mar. 4, 1980

[54] AMIDES OF LEUROSINE, LEUROFORMINE, DESACETYLLEUROSINE AND DESACETYLLEUROFORMINE

[75] Inventors: Robert A. Conrad, Indianapolis; George J. Cullinan, Trafalger; Jean C. Miller; Koert Gerzon, both of Indianapolis, all of Ind.

[73] Assignee: Eli Lilly and Company, Indianapolis, Ind.

[21] Appl. No.: 914,695

[22] Filed: Jun. 12, 1978

Related U.S. Application Data

[63] Continuation-in-part of Ser. No. 822,464, Aug. 8, 1977, abandoned.

[51] Int. Cl.$^2$ .............................................. C07D 519/04
[52] U.S. Cl. ................................... 260/244.4; 424/258
[58] Field of Search ................... 260/287 B; 424/258, 424/262

[56] References Cited

U.S. PATENT DOCUMENTS 4,144,237  3/1979  Kutney .............................. 260/244.4

FOREIGN PATENT DOCUMENTS 2558027  7/1976  Fed. Rep. of Germany.
2558124  7/1976  Fed. Rep. of Germany.

*Primary Examiner*—David E. Wheeler
*Attorney, Agent, or Firm*—James L. Rowe; Arthur R. Whale

[57] ABSTRACT

C-3 Carboxamides of leurosine, leuroformine, 4-desacetylleurosine and 4-desacetylleuroformine, useful as antitumor agents.

6 Claims, No Drawings

AMIDES OF LEUROSINE, LEUROFORMINE, DESACETYLLEUROSINE AND DESACETYLLEUROFORMINE

CROSS-REFERENCE

This application is a continuation-in-part of our copending application Ser. No. 822,464 filed Aug. 8, 1977, now abandoned.

BACKGROUND OF THE INVENTION

Several naturally-occurring alkaloids obtainable from *Vinca rosea* have been found active in the treatment of experimental malignancies in animals. Among these are leurosine (U.S. Pat. No. 3,370,057), vincaleukoblastine (vinblastine) to be referred to hereinafter as VLB (U.S. Pat. No. 3,097,137), leurosidine (vinrosidine) and leurocristine (VCR or vincristine) (both in U.S. Pat. No. 3,205,220), deoxy VLB "A" and "B", *Tetrahedron Letters*, 783 (1968) (desacetyl leurosine hydrazide is also disclosed therein); 4-desacetoxy vinblastine (U.S. Pat. No. 3,954,773); 4-desacetoxy-3'-hydroxyvinblastine (U.S. Pat. No. 3,944,554); leurocolombine (U.S. Pat. No. 3,890,325), leuroformine (N-formylleurosine), see Belgian Pat. No. 811,110) and vincadioline (U.S. Pat. No. 3,887,565). Two of these alkaloids, VLB and vincristine, are now marketed as drugs for the treatment of malignancies in humans, particularly the leukemias and related diseases.

The more abundant dimeric indole-dihydroindole alkaloids obtainable from *Vinca rosea* can be represented by the formula:

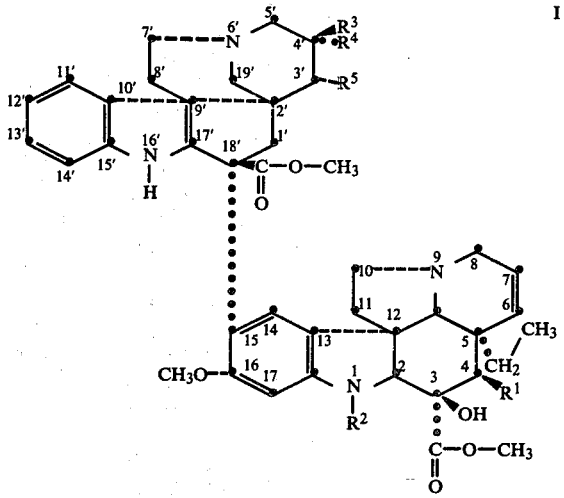

I

In the above formula where $R^1$ is acetoxy, $R^2$ is methyl, $R^3$ is hydroxyl, $R^4$ is ethyl and $R^5$ is H, VLB is represented; where $R^1$ is acetoxy, $R^2$ is formyl, $R^3$ is hydroxyl, $R^4$ is ethyl and $R^5$ is H, vincristine is represented; where $R^1$ is acetoxy, $R^2$ is methyl, $R^3$ is ethyl, $R^4$ is hydroxyl and $R^5$ is H, leurosidine is represented; where $R^1$ is acetoxy, $R^2$ is methyl, $R^3$ and $R^5$ are H and $R^4$ is ethyl, deoxy VLB "A" is represented; where $R^1$, $R^2$ and $R^5$ are the same as in deoxy VLB "A" but $R^3$ is ethyl and $R^4$ is hydrogen, deoxy VLB "B" is represented; and where $R^1$ is acetoxy, $R^2$ is methyl, $R^3$ is ethyl and $R^4$ and $R^5$ taken together form an α-epoxide ring, leurosine is represented.

Leuroformine has the same structure as leurosine except that $R^2$ is formyl, not methyl. Leurocolombine and vincadioline are 2'-hydroxy VLB and 3'-hydroxy VLB respectively; 4-desacetoxy VLB has the same structure as VLB except that $R^1$ is H rather than acetoxy; and 3'-hydroxy-4-desacetoxy VLB could also be called 4-desacetoxy vincadioline.

Chemical modification of the Vinca alkaloids has been rather limited. In the first place, the molecular structures involved are extremely complex and chemical reactions which affect only one specific function of the molecule are difficult to develop. Secondly, alkaloids lacking desirable chemotherapeutic properties have been recovered from *Vinca rosea* fractions, and a determination of their structures has led to the conclusion that these compounds are closely related to the active alkaloids. Thus, anti-neoplastic activity seems to be limited to very specific structures, and the chances of obtaining more active drugs by modification of these structures would seem to be correspondingly slight. Among the successful modifications of physiologically-active alkaloids has been the preparation of dihydro VLB (U.S. Pat. No. 3,352,868) and the replacement of the acetyl group at C-4 (carbon no. 4 of the VLB ring system—see the numbered structure above) with higher alkanoyl groups or with unrelated acyl groups. (See U.S. Pat. No. 3,392,173.) Several of these derivatives are capable of prolonging the life of mice inoculated with P1534 leukemia. One of the derivatives in which a chloracetyl group replaced the C-4 acetyl group of VLB was also a useful intermediate for the preparation of structurally modified VLB compounds in which for example an N,N-dialkylglycyl group replaced the C-4 acetyl group of VLB (see U.S. Pat. No. 3,387,001). An intermediate compound, namely 4-desacetyl VLB, was produced during the chemical reactions leading to these latter derivatives. This intermediate, in which the C-4 acyl group was lacking, leaving an unesterified hydroxyl group, was reported to be a toxic material having little in vivo chemotherapeutic activity against the P1534 murine leukemia system by Hargrove, *Lloydia*, 27, 340 (1964). More recent work, however, has shown 4-desacetyl VLB to be an active anti-tumor agent—see Owellen *Fed. Proc.* 34, 808 (1975) and Cullinan et. al., 9th International Congress of Chemotherapy, London, 1975, Abstract SC-19.

One of the more recent, and successful, chemical modifications of the dimeric indole-dihydroindole alkaloids from vinca has been the replacement of the C-3 ester function with an amide or hydrazide function usually with the concomitant loss of the acetyl at C-4 (which group can be replaced). Amides of the alkaloids VLB, leurosidine, vincristine, deoxy VLB "A" and "B", leurocolombine, vincadioline, 4-desacetoxy VLB, 3'-hydroxy-4-desacetoxy VLB, etc. are disclosed in Belgian Pat. No. 837,390.

Two of the above alkaloids, VLB and vincristine, are now marketed for the treatment of malignancies in humans and two others, leuroformine and 4-desacetyl VLB C-3 carboxamide (vindesine) are now on clinical trial in Europe or the United States as potential "anti-cancer" drugs.

It is an object of this invention to convert the relatively abundant alkaloid leurosine to structures having greater antimitotic action.

SUMMARY OF THE INVENTION

In fulfillment of the above and other objects, this invention provides compounds represented by the following formula:

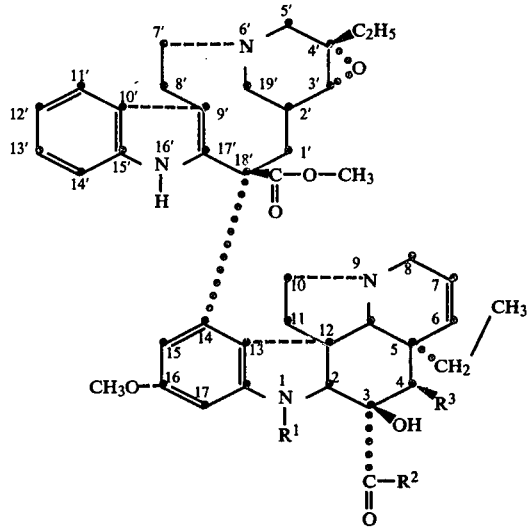

wherein $R^1$ is H, $CH_3$ or CHO; $R^2$ is $NH_2$, $N_3$, NH-alk, or NH—$CH_2$—$(CH_2)_n$X wherein n is 1 or 2 and X is OH, O-alk, O—CO-alk or SY wherein Y is H, alk or a bond, said bond joining two moieties of the above formula (II) thru the C-3 carboxamido ($R^2$) group when $R^2$ is NH—$CH_2$—$(CH_2)_n$—X, n is 1 or 2, X is SY, and Y is a bond,, and $R^3$ is OH or acetoxy. The term "alk" as used herein is defined as ($C_1$–$C_3$) alkyl and includes methyl, ethyl, n-propyl and isopropyl. Pharmaceutically-acceptable acid addition salts of the above alkaloidal bases are also included within the scope of this invention.

In formula II above, when $R^1$ is methyl, and $R^3$ is OH, C-3 carboxamides of 4-desacetylleurosine are represented and when $R^1$ is CHO, and $R^3$ is OH, C-3 carboxamides of 4-desacetylleuroformine. Compounds according to Formula II in which $R^1$ is H or $CH_3$, $R^2$ is azide or hydrazide and $R^3$ is hydroxy or acetoxy are primarily, if not exclusively, useful as intermediates as will be shown hereinafter.

Non-toxic acids useful for forming pharmaceutically-acceptable acid addition salts of the compounds of this invention include salts derived from inorganic acids such as: hydrochloric acid, nitric acid, phosphoric acid, sulfuric acid, hydrobromic acid, hydriodic acid, nitrous acid, phosphorous acid and the like, as well as salts of non-toxic organic acids including aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include the sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, 2-hydroxybutyrate, glycollate, malate, tartrate, methanesulfonate, propanesulfonate, naphthalene-1-sulfonate, naphthalene-2-sulfonate and the like salts.

Illustrative compounds coming within the scope of this invention include:

4-desacetylleuroformine C-3 N-(β-methoxyethyl)carboxamide, leurosine C-3 N-(β-isopropoxyethyl)carboxamide, 4-desacetylleuroformine C-3 N-(β-methylmercaptoethyl)carboxamide, leurosine C-3 N-(β-mercaptoethyl)carboxamide, 4-desacetylleuroformine C-3 N-methylcarboxamide, 4-desacetylleurosine C-3 N-(β-ethoxyethyl)carboxamide, leuroformine C-3 N-(β-hydroxyethyl)carboxamide, and 4-desacetylleurosine C-3 N-(β-n-propoxyethyl)carboxamide.

Suitable starting materials for the preparation of the oncolytic compounds of this invention represented by Formula II (exclusive of those in which $R^1$ is H or $CH_3$ and $R^2$ is NH-$NH_2$ or $N_3$) are 4-desacetylleurosine C-3 carboxhydrazide or 1-desformyl-4-desacetylleuroformine C-3 carboxhydrazide. Conversion of these hydrazides to the corresponding azide by treatment with nitrous acid followed by reaction with ammonia or a particular desired primary amine including methyl amine, β-hydroxyethylamine, a β-($C_1$-$C_3$ alkylmercapto) ethyl (or propyl) amine yields a 4-desacetyl C-3 carboxamide (II when $R^1$ is $CH_3$ and $R^3$ is OH) or a 4-desacetyl-1-desformyl C-3 carboxamide (II when $R^1$ is H and $R^3$ is OH). This hydrazide-azide-amide transformation follows the procedure originated by Stohl and Huffman, *Helv. Chim. Acta.*, 26, 944 (1943)—see also U.S. Pat. Nos. 2,090,429 and 2,090,430.

Compounds in which the amide group contains an ester function as in the group NH—$CH_2$—$CH_2$—O—CO-alk, wherein alk is as defined above, are preferably prepared by esterifying the hydroxyethyl (or propyl) amide with a suitable acid anhydride (alk-CO)$_2$O.

Compounds in which $R^2$ is NH—$CH_2$—$CH_2$—SH can be prepared by reaction of 4-desacetylleurosine C-3 carboxazide with β-mercaptoethylamine. The mercaptan, however, undergoes oxidation under alkaline reaction conditions to yield the corresponding disulfide: DAL—CO—NH—$C_2H_4$—S—S—$C_2H_4$—NH—CO—DAL where DAL—CO is the 4-desacetylleurosine C-3 carboxy radical. Using the standard azide synthetic procedure the mercaptoethylamides and their corresponding disulfides are usually isolated as a mixture readily separable by chromatography. A synthesis of the mercaptoethylamide free from accompanying disulfide involves the reaction of a C-3 carboxazide with $NH_2$—$CH_2$—$CH_2$—S-trityl, where trityl is a triphenylmethyl group. Treatment of the C-3 N-tritylmercaptoethyl carboxamide with a heavy metal salt such as mercuric acetate followed by removal of the metal salt as an insoluble sulfide yields the desired mercaptoethylamide ($R^2$ is NH—$CH_2$—$CH_2$—SH) substantially free from disulfide. Tris substituted triphenylmethyl derivatives can also be used as blocking groups. The disulfide is prepared unambiguously by the reaction of 2 moles of 4-desacetylleurosine C-3 carboxazide and cystamine (NH$_2$—CH$_2$—CH$_2$—S)$_2$. The mercaptopropyl amide and corresponding disulfide are prepared analogously.

One way of preparing the compounds of this invention wherein R$^3$ is acetoxy, is to reacetylate a 4-desacetyl amide (II wherein R$^3$ is OH) with acetic anhydride or acetyl chloride in pyridine to yield the corresponding C-4 acetate. The preferred acetylation procedure is that described in U.S. Pat. No. 3,392,173 for VLB or leurocristine in which a diacyl derivative is the first product of the reaction, and this derivative is selectively hydrolysed to yield a 4-acetoxy compound. Other procedures involving selective acetylation or multiple acetylation followed by selective hydrolysis can be employed to prepare the 4-acetoxy derivatives of this invention.

There are, however, certain provisos which must be kept in mind when an acetylation procedure is contemplated. If the C-3 carboxamide group contains an acylable group; i.e., hydroxy or amino, the C-4 acetylation procedure must be carried out prior to the azide-amine reaction which yields the ultimate C-3 carboxamide group. The preferred procedure here is to acylate at C-4, by the above procedures, a C-3 carboxhydrazide, first protecting the hydrazide group itself, which would otherwise also be acetylated. The preferred hydrazide protecting group is the isopropylidene group formed by reaction of the NH$_2$ portion of the hydrazide moiety with acetone. This group can be readily removed by treatment with acid or, preferably, the isopropylidene derivative itself can be reacted directly with nitrous acid to form an azide group (see U.S. Pat. No. 3,470,210, Example VII). In addition, the 4-acetoxy C-3 carboxazide thus prepared undergoes reaction with NH$_3$ and various primary amines to yield compounds having the desired R$^2$ amide group.

Other procedures involving selective acetylation or multiple acetylation followed by selective hydrolysis or selective protection of an acetylatable function followed by acetylation and subsequent removal of the protecting group will be apparent to those skilled in the art.

Preparation of leuroformine C-3 carboxamides involves some added considerations. Reaction of leuroformine with hydrazine not only forms a C-3 carboxhydrazide but also hydrolyses both the C-4 acetyl and N-1 formyl groups. Thus, the usual starting material for preparing either a leuroformine or a 4-desacetylleuroformine C-3 carboxamide is 4-desacetyl-1-desformylleuroformine C-3 carboxhydrazide. This compound can be converted to the corresponding azide with nitrous acid. Reaction of the azide with NH$_3$ or a suitable primary amine yields a C-3 carboxamide which must be reformylated to yield a 4-desacetylleuroformine C-3 carboxamide or reacetylated and reformylated to yield a leuroformine C-3 carboxamide of this invention (Formula II). Alternatively, a leurosine or 4-desacetylleurosine C-3 carboxamide can be oxidized at $-60°$ C. in acetone-acetic acid with CrO$_3$ (Jovanovics, et al. procedure of U.S. Pat. No. 3,899,493) to yield the N-1 formyl derivative directly (Formula II, R$^1$ is CHO) or an N-1 desformyl compound (II, R$^1$ is H) which can in turn be reformylated. This procedure may not be suitable for amides containing oxidizable groups, although routine CrO$_3$ oxidations proceed very slowly if at all at $-60°$ C.

The alkaloidal bases of this invention and their acid addition salts, in particular the sulfate salts, are white crystalline solids. Leurosine, which is the ultimate starting material for the preparation of the compounds of this invention, is obtained from *Vinca rosea* by the procedures set forth in U.S. Pat. Nos. 3,370,057 and 3,225,030. Leurosine, upon standing in air, auto-oxidizes to a 5'-hydroxy derivative. Thus, when leurosine is to be employed as a starting material in a reaction, a preliminary leurosine purification step is necessary. This procedure can be carried out as follows:

150 g. of crude leurosine containing about 50 percent 5'-hydroxyleurosine is heated for one hour in 4 l. of ethanol. The ethanol solution is cooled and the resulting crystalline material—80 g.—is separated by filtration. The crystalline material is then dissolved in methylene dichloride and the methylene dichloride solution chromatographed over 1.5 kg. of silica. The chromatogram is developed with a 2:1:2 ethyl acetate/methanol/methylene dichloride solvent mixture. Early eluate fractions shown to contain 5'-hydroxyleurosine by TLC are combined to yield 24 g. of purified 5'-hydroxyleurosine. Later cuts shown to contain leurosine by TLC are combined to yield 6 g. of leurosine. Intermediate cuts yielded 42 g. of a mixture of the two alkaloids from which further purified compounds can be recovered.

5'-Hydroxyleurosine is disclosed in copending application of Thompson et. al., Ser. No. 822,466, filed Aug. 8, 1977, now U.S. Pat. No. 4,122,081.

The preparation of the compounds of this invention is illustrated in the following specific examples:

EXAMPLE 1

Preparation of 4-Desacetylleurosine C-3 Carboxhydrazide

A reaction mixture containing 450 mg. of leurosine, 15 ml. of tetrahydrofurane (THF), 8 ml. of anhydrous hydrazine, and 6 ml. of methanol were heated in a sealed glass bomb for 3 days at 50° C. The bomb was opened, the solvents removed in vacuo, and the resulting residue comprising 4-desacetylleurosine C-3 carboxhydrazide formed in the above reaction, was dissolved in methylene dichloride. The methylene dichloride solution was washed with water and dried. Removal of the solvent in vacuo yielded 4-desacetylleurosine C-3 carboxhydrazide as a residue shown by TLC to contain trace quantities of leurosine and of 4-desacetylleurosine. Pure 4-desacetylleurosine C-3 carboxhydrazide (1-spot material) was prepared by chromatographing the residue over silica using 1:1:1 methylenedichloride/ethyl acetate/methanol as the eluant. Fractions shown by TLC to contain 4-desacetylleurosine C-3 carboxhydrazide were combined. The compound had the following physical characteristics: Mass spectrograph: m/e 766 (molecular ion) 649,427; infrared (chloroform) peaks at 3480, 3440, 1730 and 1670 cm$^{-1}$; pKa's (in 66 percent DMF) at 5.32 and 7.12.

EXAMPLE 2

Preparation of 4-Desacetylleurosine C-3 Carboxazide

Approximately 800 mg. of 4-desacetylleurosine C-3 carboxhydrazide were dissolved in 120 ml. of 1 N aqueous hydrochloric acid which has previously been cooled to 0° C. 180 mg. of sodium nitrite were added and the reaction mixture stirred for 10 minutes at 0° C. The acidic aqueous solution was made basic with aqueous sodium bicarbonate solution and the alkaline solution extracted twice with chloroform. The chloroform extracts were separated and combined and the combined extracts dried. Evaporation of the chloroform yielded 4-desacetylleurosine C-3 carboxazide as a tan

EXAMPLE 3

Preparation of 4-Desacetylleurosine C-3 Carboxamide

A methylene dichloride solution of the 4-desacetylleurosine C-3 carboxazide from Example 2 was added to 250 ml. of methylene dichloride which had previously been saturated with gaseous ammonia at 10° C. The reaction vessel was fitted with a drying tube and the reaction was protected from light. The reaction mixture was maintained at room temperature over night and the volatile constituents then removed by evaporation in vacuo. The resulting residue, containing 4-desacetylleurosine-C-3 carboxamide formed in the above reaction, was dissolved in methylene dichloride, and the methylene dichloride solution washed twice with water and dried. Chromatography over silica gel using a 3:1 ethyl acetate/ethanol solvent mixture as the eluant yielded fractions containing purified 4-desacetylleurosine C-3 carboxamide as determined by TLC. These fractions were combined and the solvent removed therefrom by evaporation in vacuo. 4-Desacetylleurosine C-3 carboxamide was obtained as a tan amorphous powder with the following physical characteristics: Mass spectrograph (m/e): molecular ion=751, also peaks at 692, 649, and 412. Infrared spectrum: peaks at 3520, 3485, 3410, 1740, and 1695 cm$^{-1}$.

EXAMPLE 4

Preparation of 4-Desacetylleurosine C-3 N-($\beta$-hydroxyethyl)carboxamide

Following the procedure of Example 3, 4-desacetylleurosine C-3 carboxazide was reacted with ethanolamine in methylene dichloride to yield 4-desacetyl C-3 N-($\beta$-hydroxyethyl)carboxamide.

The compound was purified by chromatography over silica gel using a 1:1 ethyl acetate/methanol eluant. The resulting tan amorphous powder had the following physical characteristics: molecular spectrum (m/e): molecular ion at 795; infrared spectrum: peaks at 3480, 3410, 1735 and 1670 cm$^{-1}$.

EXAMPLE 5

Preparation of 4-Desacetylleurosine C-3 N-Methyl Carboxamide

About 0.25 g. of leurosine sulfate were converted to the free base by dissolving the salt in water and making the resulting solution alkaline. The free base was insoluble in the aqueous alkaline layer and was extracted with chloroform. Evaporation of the chloroform yielded leurosine free base as a residue.

Leurosine free base (corresponding to 0.25 g. of leurosine sulfate) thus prepared was dissolved in 100 ml. of anhydrous methanol to which had been added 21 g. of methylamine at −78° C. The reaction vessel was sealed and heated at 50° C. for 5 days. The reaction vessel was opened and the volatile constituents removed by evaporation in vacuo. The resulting residue comprising 4-desacetylleurosine C-3 N-methyl carboxamide formed in the above reaction was dissolved in methylene dichloride. The methylene dichloride solution was washed 3 times with water and then dried. Evaporation of the methylene dichloride yielded 4-desacetylleurosine C-3 N-methyl carboxamide as a powder, a solution of which was chromatographed over preparative thin-layer chromatography silica gel plates. The chromatogram was developed with a 1:1 ethyl acetate/ethanol solvent mixture. A band corresponding to 4-desacetylleurosine C-3 N-methyl carboxamide was removed manually and the alkaloid eluted from the silica gel with methanol. Evaporation of the methanol yielded 4-desacetylleurosine C-3 N-methyl carboxamide as a tan amorphous powder having the following physical characteristics: molecular spectrum (m/e): 765 (molecular ion), 779 (molecular ion+14) 607, 426, 353; infrared spectrum: peaks at 2.84, 5.75, and 5.97 microns.

EXAMPLE 6

Alternate Preparation of 4-Desacetylleurosine C-3 N-methyl Carboxamide

Following the procedure of Example 3, 4-desacetylleurosine C-3 N-methyl carboxamide was prepared from methylamine and 4-desacetylleurosine C-3 carboxazide in methylene dichloride.

EXAMPLE 7

Preparation of 4-Desacetylleurosine C-3 N-($\beta$-mercaptoethyl)carboxamide

Following the procedure of Example 3, 2-mercaptoethylamine was reacted with 4-desacetylleurosine C-3 carboxazide in methylene dichloride. The $\beta$-mercaptoethylamine was prepared by dissolving its hydrochloride salt in 1 N aqueous sodium hydroxide, saturating the aqueous layer with sodium chloride and extracting the aqueous layer twice with each of the following solvents: ethyl acetate, ether and methylene dichloride. The 6 extracts were combined, dried, and filtered and the solvents removed by evaporation. The azide-$\beta$-mercaptoethylamine mixture in methylene dichloride was heated to reflux temperature on the steam bath for 5 minutes and then cooled. 5 ml. of pyridine were added and the reaction mixture stirred at ambient temperature overnight. 5 Percent aqueous sodium bicarbonate solution was added and the organic and aqueous layers separated. The organic layer was washed twice with water and dried. Removal of the solvent in vacuo left as a residue a mixture of 4-desacetylleurosine C-3 N-($\beta$-mercaptoethyl)carboxamide and bis[$\beta$-(4-desacetylleurosine C-3 carboxamido)ethyl]disulfide. The residue was dissolved in methylene dichloride, the methylene dichloride solution washed three times with water, and the solvent removed by evaporation in vacuo. The residue comprising the above mixture was chromatographed over silica and the chromatogram developed with a 1:1:1 methylene dichloride/ethyl acetate/methanol solvent mixture. Fractions shown by TLC to contain 4-desacetylleurosine C-3 N-($\beta$-mercaptoethyl) carboxamide were combined and the solvents removed therefrom in vacuo. 4-Desacetylleurosine C-3 N-($\beta$-mercaptoethyl) carboxamide was a tan amorphous solid with the following physical characteristics: molecular spectrum (m/e): 825, (molecular ion+14)-transmethylation), 486, 353, 299, 152. Infrared spectrum (in chloroform); peaks at 1730 and 1665 cm$^{-1}$. Fractions shown to contain bis[$\beta$-(4-desacetylleurosine C-3 carboxamido)ethyl]disulfide were combined and the solvents evaporated therefrom. The residue was a tan amorphous solid having substantially the same physical characteristics as the mercaptan given in Example 9.

EXAMPLE 8

Preparation of 4-Desacetylleuroformine C-3 Carboxamide

A solution was prepared from 3.4 g. of 4-desacetyl-leurosine C-3 carboxamide, 40 ml. of methylene dichloride and 450 ml. of acetone. The solution was cooled to −61° C. and 50 ml. of glacial acetic acid were added. Next, a solution of 4 g. of chromic oxide in 8 ml. of water and 40 ml. of glacial acetic acid was added over a period of 20 minutes. After the addition had been completed, the solution was stirred for an additional hour at −61° C. and was then allowed to warm to −30° C. The reaction mixture was held at this temperature for one hour and then again cooled to −61° C. 14 N Ammonium hydroxide and water were added. The organic layer was separated and the aqueous layer washed three times with methylene dichloride. The methylene dichloride extracts were combined, washed once with water, and dried. Evaporation of the solvent yielded a residue which was separated into its components by chromatography over silica using 1:1:1 methylene dichloride/methanol/ethyl acetate as an eluant. Two components were detected. The faster moving one was indicated by NMR to be 5'-acetonyl-4-desacetyl-leuroformine C-3 carboxamide and the slower, more polar, compound as indicated by NMR to be 4-desacetylleuroformine C-3 carboxamide. 4-Desacetyl-leuroformine C-3 carboxamide had the following physical characteristics: Mass spectrum (m/e)=765 (FD); IR (CHCl$_3$) 1730, 1680 cm$^{-1}$.

5'-Acetonyl-4-desacetylleuroformine C-3 carboxamide, the second component, had the following physical characteristics: Mass spectrum (m/e)=821 (FD); NMR similar to 4-desacetyl-leuroformine C-3 carboxamide with extra peak at δ2.12 (acetonyl methyl); IR (CHCl$_3$) 1730, 1680 cm$^{-1}$.

EXAMPLE 9

Preparation of Bis[β-(4-desacetylleurosine C-3 carboxamido)ethyl]disulfide

Five grams of 4-desacetylleurosine C-3 carboxhydrazide were converted to the corresponding C-3 carboxazide by the procedure of Example 2 using 250 ml. of 1 N HCl and 500 mg. of NaNO$_2$. The azide was isolated as a solution in methylene dichloride. To this solution was added 450 mg. of cystamine (NH$_2$—CH$_2$—CH$_2$—S)$_2$ in 20 ml. of THF. The reaction mixture was stirred at ambient temperature overnight, and was then worked up as in Example 3. The residue obtained, comprising bis[β-(4-desacetylleurosine C-3 carboxamido)ethyl]disulfide formed in the above reaction, was purified by chromatography over silica gel using a 1:1:1 methylene dichloride/ethyl acetate/methanol solvent mixture as the eluant.

Fractions shown to contain the disulfide by TLC were combined, and the solvents evaporated therefrom. The residue was converted to the disulfate salt by the procedure of Example 12 below. The free base had the following physical characteristics: Mass spectrum; peaks at 825, 839, 486; infrared spectrum: ν=1730, 1670 cm$^{-1}$;

$^{13}$C nmr; extra resonances at 37.5, 39.2, ppm.
as compared with 4-desacetylleurosine C-3 carboxamide.
Titration; pK$_a$ at 5.3, 7.0
Osmotic molecular weight; 1479.

EXAMPLE 10

Preparation of Salts

Sulfate salts of the above amides are prepared by dissolving the particular amide in absolute ethanol and adjusting the pH of the resulting solution to about 4.5 with 2 percent ethanolic sulfuric acid. Other salts, including salts with inorganic ions such as chloride, bromide, phosphate, nitrate and the like as well as salts with organic ions such as benzoate, methanesulfonate, maleate, tartrate and the like are prepared in analogous fashion.

The compounds of this invention are active against transplanted tumors in mice in vivo and induce metaphase arrest in Chinese hampster ovary cells maintained in tissue culture in a procedure adapted from that of Siminoff, *Applied Microbiology*, 9, 66–72 (1961).

In demonstrating activity of the drugs of this invention against transplanted tumors in mice, a protocol was used which involved the administration of the drug, usually by the intraperitoneal route, at 12,6 and 3 mg/kg per day for 9 days after innoculation with the tumor.

The following table—Table 1—gives the results of experiments in which mice bearing transplanted Gardner lymphosarcoma were treated successfully with a compound of this invention. In the table, column 1 gives the name of the compound; column 2, the dose level and column 3, the percent inhibition of tumor growth.

Bis[β-(4-desacetylleurosine C-3 carboxamide)ethyl]-disulfide disulfate was active against the P388 leukemia in mice, when administered at the 15 and 30 mg/kg level on three occasions, 3 days apart. 55 and 46 percent prolongation of survival time respectively were observed.

In utilizing the novel compound of this invention as anti-tumor agents in mammals, the parenteral route of administration is conveniently employed. With parenteral administration, the intravenous route is preferred although with smaller mammals such as mice the intraperitoneal route may be used. For intravenous administration, isotonic solutions are employed containing 1–10 mg./ml. of a salt of an alkaloidal base of formula II alone. The compounds are administered at a rate of from 0.01 to 1 mg./kg. and preferably from 0.1 to 1 mg./kg. of mammalian body weight once or twice a week or every two weeks depending on both the activity and the toxicity of the drug. An alternative method of arriving at a therapeutic dose is based on body-surface area with a dose in the range 0.1 to 10 mg./meter squared of mammalian body surface every 7 or 14 days.

TABLE 1

| Activity versus Gardner Lymphosarcoma | | |
|---|---|---|
| Compound | Dose mg/kg. | Percent Inhibition |
| 4-desacetylleurosine C-3 carboxamine | 12 | Toxic |
|  | 6 | 100 |
|  | 3 | 23 |
| 4-desacetulleurosine C-3 N-methyl carboxamide | 12 | Toxic |
|  | 6 | 100 |
|  | 3 | 33 |
| 4-desacetylleurosine C-3 N-(β-hydroxyethyl) carboxamide | 12 | 100, 98 |
|  | 6 | 100, 100 |
|  | 3 | 11 50, 44 |
| 4-desacetylleuroformine C-3 carboxamide | 12 | 39 |

We claim:

1. A compound of the formula:

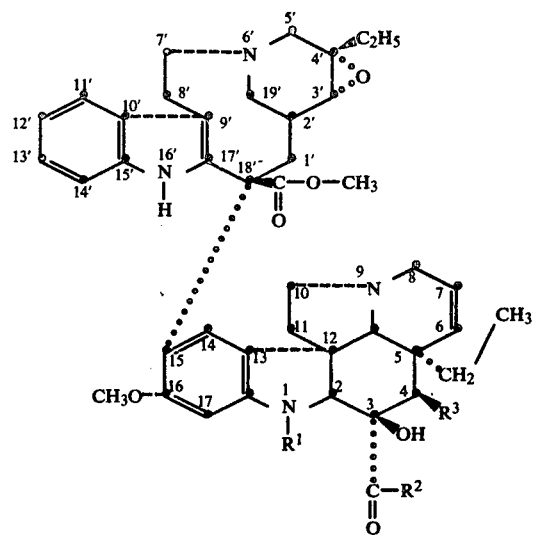

wherein $R^1$ is $CH_3$ or CHO; $R^2$ is $NH_2$, $NH-CH_3$, or $NH-CH_2-CH_2-X$, wherein X is OH or SY wherein Y is $CH_3$ or a bond, said bond joining two moieties of the above formula thru the C-3 carboxamido group when $R^2$ is $NH-CH_2-CH_2-X$, X is SY and Y is a bond; and $R^3$ is OH; and pharmaceutically-acceptable acid addition salts thereof.

2. A compound according to claim 1, said compound being 4-desacetylleuroformine C-3 carboxamide.

3. A compound according to claim 1, said compound being 4-desacetylleurosine C-3 carboxamide.

4. A compound according to claim 1, said compound being 4-desacetylleurosine C-3 N-methylcarboxamide.

5. A compound according to claim 1, said compound being 4-desacetylleurosine C-3 N-(β-hydroxyethyl)carboxamide.

6. A compound according to claim 1, said compound being bis[β-(4-desacetylleurosine C-3 carboxamido)ethyl]disulfide.

* * * * *